United States Patent
Siggel et al.

(10) Patent No.: US 7,601,871 B2
(45) Date of Patent: Oct. 13, 2009

(54) METHOD FOR PURIFYING QUATERNARY ONIUM SALTS

(75) Inventors: Alfred Siggel, Seelze (DE); Michael Fooken, Seelze (DE); Michael Theissen, Hanover (DE); Andreas Kanschik-Conradsen, Garbsen (DE); Sonja Demel, Wunstorf (DE); Frank Nerenz, Hannover (DE)

(73) Assignee: Honeywell International Inc., Morristown, NJ (US)

( * ) Notice: Subject to any disclaimer, the term of this patent is extended or adjusted under 35 U.S.C. 154(b) by 232 days.

(21) Appl. No.: 11/368,168

(22) Filed: Mar. 3, 2006

(65) Prior Publication Data

US 2006/0247472 A1 Nov. 2, 2006

Related U.S. Application Data

(60) Provisional application No. 60/658,545, filed on Mar. 4, 2005.

(51) Int. Cl.
C07C 213/00 (2006.01)
(52) U.S. Cl. ..................................... 564/281
(58) Field of Classification Search ....................... None
See application file for complete search history.

(56) References Cited

U.S. PATENT DOCUMENTS

| | | | |
|---|---|---|---|
| 5,086,374 A | 2/1992 | MacFarlane et al. | 361/525 |
| 5,965,054 A | 10/1999 | McEwen et al. | 252/62.2 |
| 5,968,338 A | 10/1999 | Hulme et al. | |
| 6,207,039 B1 * | 3/2001 | Moulton et al. | 205/703 |
| 2003/0121787 A1 | 7/2003 | Reiter et al. | |

FOREIGN PATENT DOCUMENTS

| | | |
|---|---|---|
| JP | 1246386 * | 10/1989 |
| WO | 99/51529 | 10/1999 |
| WO | WO 2004/039761 | 5/2004 |

OTHER PUBLICATIONS

Hajime Katano, et al., *Voltammetric Study of the Transfer of Polyammonium Ions at Nitrobenzene | Water Interface*; vol. 20, Analytical Sciences, pp. 1581-1585 (Nov. 2004).
Sharon I. Lall, et al.; *Polycations. Part X. LIPs, a new category of room temperature ionic liquid based on polyammonium salts*, Chem. Commun., pp. 2413-2414 (2000).
Sorina Ulmeanu, et al., *Voltammetric characterisation of polyelectrolyte adsorption/transfer at the water | 1,2-DCE interface*; Electrochemistry Communications 3; pp. 539-543 (2001).

* cited by examiner

*Primary Examiner*—Karl J Puttlitz
(74) *Attorney, Agent, or Firm*—Carrie Beatus (57) ABSTRACT

Provided are methods of purifying quaternary onium salts having the steps of (a) providing an quaternary onium salt solution having a first ionic impurity concentration; (b) providing an ion exchange material charged with electrochemically stable anions; and (c) contacting the salt solution with the ion exchange material to produce an quaternary onium salt solution having a second halide concentration is less than the first ionic impurity concentration.

49 Claims, 5 Drawing Sheets

METHOD FOR PURIFYING QUATERNARY ONIUM SALTS

CROSS-REFERENCE TO RELATED APPLICATIONS

This application claims the priority of U.S. Provisional Application No. 60/658,545 filed on Mar. 4, 2005. The aforementioned provisional application is incorporated herein by reference.

FIELD OF INVENTION

The present invention relates to methods for purifying quaternary onium salts. More specifically, the present invention relates to methods for purifying quaternary onium salts containing ionic impurities, e.g. halides, as well as acidic impurities.

BACKGROUND

Quaternary onium salts are highly soluble and readily dissociate in many non-aqueous as well as aqueous solvents. This property enables many solvents, which conventionally are not considered as having the ability to support electrical conductivity, to be used as an effective electrolyte medium.

Quaternary onium cations, and in particular tetraalkylammonium cations, are relatively electrochemically stable. That is, these cations are relatively stable against electrochemical reduction processes. When these cations are combined with a similarly stable anion (i.e. stable against electrochemical oxidation processes) in a suitable solvent, the resulting electrolyte can be used in a wide variety of electrochemical applications such as carbon-based electrode supercapacitors. See e.g. U.S. Pat. No. 5,086,374, which is incorporated herein by reference.

The electrochemical stability of a substance is represented by its so called electrochemical window, possessing Volts (V) as a unit and determined by cyclic voltammetry (CV). The higher the value in Volts (or "the wider" the electrochemical window), the more stable the corresponding material is against oxidation or reduction processes. The general trend of cation stability is:

pyridinium<pyrazolium≦imidazolium≦sulfonium≦ammonium, and the trend of anion stability is:

halides (I⁻, Br⁻, Cl⁻,
F⁻)<chloroaluminates≦perfluorinated ions (e.g.
BF₄⁻, PF₆⁻, AsF₆⁻) ≦([CF₃SO₃]⁻, [(CF₃
SO₂)₂N]⁻, [(C₂F₅SO₂)₂N]⁻, [(CF₃SO₂)₃C]⁻.

The wideness of the electrochemical window is generally very sensitive to impurities, especially residual halides. Since halides are generally oxidized much easier than, for example, perfluorinated anions, halide contaminants in an electrolyte can frequently lead to significantly lower electrochemical stability.

Further "free acid" has been identified as a critical parameter, e.g. low ppm-levels of tetrafluoroboronic acid in onium tetrafluoroborate electrolytes. By applying a certain voltage to an acid containing electrolyte, the free acid equilibrates with gaseous compounds causing problems, e.g., reduced lifetimes, in the devices that use such products.

Many quaternary onium salts are commercially prepared by reacting alkylamines with alkylfluorides, alkylchlorides, alkylbromides, or alkyliodides to form alkylammonium halides. These alkylammonium halides are then converted into quaternary onium salts essentially free of fluoride, chloride, bromide, or iodide via methods known in the art, such as the one described in WO 2004/039761, which is incorporated herein by reference. However, as previously stated, chloride, fluoride, bromide, and iodide anions as well as residual acid are not electrochemically stable and even residual amounts of these substances in a quaternary onium salt reduces the overall electrochemical stability of the related electrolyte. This reduction in stability, in turn, leads to a shortened lifespan of many products that utilize such electrolytes. In addition, a residual amount of fluoride anions remaining in a quaternary onium salt would also cause corrosion, thus further reducing product lifespan.

Methods for reducing the halide and acid concentration of quaternary onium salts, even to negligible levels, are known in the art. For example, multiple crystallization steps may be employed to reduce impurity concentrations to below 5 parts per million (ppm). However, these and other known processes are time-consuming or have a low yield and are, therefore, expensive. Applicants have recognized the need for a less costly method of removing impurities such as halide and acid impurities from quaternary onium salts, preferably with a purification effectiveness that is equal to or better than the effectiveness of previously known methods.

SUMMARY OF THE INVENTION

Applicants have discovered that ionic impurities such as halide and free acid can be removed from non-aqueous quaternary onium salt solutions by contacting the salt solutions with an ion exchange material that a) has been charged with anions, preferably anions that are more electrochemically stable than the halide impurities and/or b) works as a scavenger. Preferred embodiments of the present methods are generally less costly and more versatile compared to many conventional crystallization methods for separating halides from quaternary onium salts and their anhydrous solutions.

Accordingly, certain preferred embodiments of the present invention comprise (i) providing a non-aqueous solution of one or more quaternary onium salts having at least one ionic impurity, e.g. halide and/or free acid at a first concentration; (ii) providing an ion exchange material charged with anions, preferably electrochemically stable anions and/or in the free form; and (iii) contacting the salt solution with the ion exchange material to produce a non-aqueous quaternary onium salt solution having a second ionic impurity concentration, wherein the second ionic impurity concentration is lower than the first ionic impurity concentration.

DETAILED DESCRIPTION OF PREFERRED EMBODIMENTS

As described herein, methods are provided for removing ionic impurities, such as halide and free acid impurities, from liquid onium salts or onium salt solutions, preferably non-aqueous, quaternary onium salt solutions. Although applicants do not intend to necessarily be bound to any particular theory of operation, it is believed that when these liquid salts or salt solutions are brought into contact with an ion-exchange material that has been charged with anions more electrochemically stable than the halide impurities, the material tends to adsorb such halide ions and thereby purify the material. Furthermore, applicants have found that this favorable result can be obtained even if the more electrochemically stable anions are present in a concentration substantially greater than, or even up to several orders of magnitude greater, than the halide anions. Thus, even though ion exchange reactions are generally reversible reactions possessing some equilibrium conditions, in the preferred aspects of the present methods these conditions are minimized so that a significant reduction, and in certain embodiments substantial elimination, of halides from the salt solution is achieved. It is further believed that the described ion exchange resins being used without anion charge tend to adsorb acidic impurities, even though the scavenger process is carried out under non-aqueous conditions.

Accordingly, one preferred step of the present invention is providing a non-aqueous quaternary onium salt solution having a first concentration of ionic impurities, like halides and/or free acid.

By the term "quaternary onium salt" it is meant a salt having a cation that can be represented as $(R^a R^b R^c R^d)A^+$, wherein A is P or N and $R^a$, $R^b$, $R^c$, and $R^d$ are, independently of each other, a $C_1$-$C_{12}$ alkyl, a member of a $C_2$-$C_{20}$ unsaturated heterocyclic, or a single, double, or non-localized pi bond, provided that a combination of bonds result in a tetravalent N or P.

The term "salt", as used herein, includes both the crystalline structure of the compound as well as the compound when it is dissolved in a solvent.

The term "salt solution" as used herein, means solution having at least one salt that is at least partially dissolved in a solvent.

The term "liquid onium salt" as used herein, means a salt that can be at least partly dissociated without the use of a solvent. For example, some quaternary onium salts described herein have such low melting points that they are liquid at room temperature and also partly dissociated and therefore conductive without any other material (such as a solvent) being present. Such liquid salts are also referred to in the art as "Ionic Liquids".

The term, "onium salt", as used herein, is not limited to a compositions of a singular onium salt, but can include a plurality of different onium salts.

By the term "halide", it is meant an ion of fluoride, chloride, bromide, iodide, or some combination thereof. By the term "free acid", it is meant a proton, usually present as dissociated proton with a counter ion or in the form of a non-dissociated acid molecule.

Preferably, quaternary onium salts according to the present invention are selected based upon their electrical conductivity, solubility, and electrochemical stability. Quaternary onium salts that may be practiced with the present invention preferably have the formula $[A^+R_4][Z^-]$, wherein A is trivalent atom such as nitrogen or phosphorous; R is independently a substituted or un-substituted $C_1$-$C_{12}$ alkyl, a substituted or un-substituted fluoroalkyl, or a member of a 5- or 6-member saturated, unsaturated, or aromatic cyclic or heterocyclic, or a member of a polycyclic structure. Particularly preferred are quaternary onium salts according to Formula I, II, III, or IV:

(I)

(II)

(III)

(IV)

wherein
A is nitrogen or phosphorous; n and m are independently 0 or 1;

_Any_ is a single, double, or aromatic bond;

$R_1$-$R_4$, $R_{10}$, $R_{15}$, $R_{24}$, and $R_{25}$ are independently a substituted or unsubstituted $C_1$-$C_{12}$ alkyl, substituted or unsubstituted fluoroalkyl, member of a five or six member saturated, unsaturated, or aromatic cyclic or heterocyclic structure, or member of a polycyclic structure (e.g., spiro-, condensated-, or bridged-structure, or some combination thereof);

$R_5$-$R_9$, $R_{11}$-$R_{14}$, $R_{16}$-$R_{23}$ are independently H, F, Cl, substituted or unsubstituted $C_1$-$C_{12}$ alkyl, substituted or unsubstituted fluoroalkyl, member of a five or six member saturated, unsaturated, or aromatic cyclic or heterocyclic structure, or member of a polycyclic structure (e.g., spiro-, condensated-, or bridged-structure, or some combination thereof);

$D_1$-$D_9$ are independently carbon, nitrogen, sulfur, or oxygen provided that:
at least three of $D_1$-$D_5$ are carbon;
at least two of $D_6$-$D_9$ are carbon;

when a D ring member is carbon, n is 1 for its corresponding R group;

when a D ring member is nitrogen, oxygen, or sulfur, n is 0 for its corresponding R group;

the bond between any two adjacent D members is single, double, or aromatic;

the bond between A and either of its two adjacent D members is single, double, or aromatic provided that A is tetravalently bonded;

$D_{10}$-$D_{13}$ are independently carbon, nitrogen, sulfur, or oxygen provided that:

at least two of $D_{10}$-$D_{13}$ are carbon;

when a D ring member is carbon, n and m are 1 for their corresponding R groups;

when a D ring member is nitrogen, n is 1 and m is 0 for their corresponding R groups;

when a D ring member is oxygen or sulfur, n and m are 0 for their corresponding R groups;

Z is a negatively charged, electrochemically stable anion, such as for example, $BF_4^-$, $[BF_x(C_yF_{2y+1-z}H_z)_{4-x}]_n^-$ in which the ligands $(C_yF_{2y+1-z}H_z)$ may be identical or different, $1<x<3$, $1 \leq y \leq 8$ and $0 \leq z \leq 2y+1$, $PF_6^-$, $[PF_x(C_yF_{2y+1-z}H_z)_{6-x}]^-$ in which in which the ligands $(C_yF_{2y+1-z}H_z)$ may be identical or different, $1 \leq x \leq 5$, $3 \leq y \leq 8$ and $0 \leq z \leq 2y+1$, $CF_3SO_3^-$, $SbF_6^-$, $N(SO_2CF_3)_2^-$, $C_4H_3O_4^-$, $ClO_4^-$, and the like.

Compounds of the structure in Formula I are quaternary onium salts that, when dissolved in a solvent, preferably form a cation having a central nitrogen or phosphorous atom joined by four organic groups and a negatively charged, electrochemically stable anion. In certain embodiments, the organic groups attached to the central atom are independently $C_1$-$C_{12}$ alkyls, or $C_1$-$C_{12}$ fluoroalkyls. Examples of the alkyl groups that constitute the quaternary alkyl ammonium cation are: a methyl group, ethyl group, n-propyl group, isopropyl group, n-butyl group, isobutyl group, sec-butyl group, tert-butyl group, n-pentyl group, isopentyl group, neopentyl group, n-hexyl group, isohexyl group, n-decyl group, n-dodecyl group, n-octadecyl group, cyclopentyl group, cyclohexyl group, and the like; and, those in which one, or two or more, hydrogen atoms comprising this unsubstituted alkyl group are substituted with a substituent such as fluorine, e.g trifluoromethyl or 2,2,2 trifluoroethyl groups; an aryl group, for example, phenyl and the like, an amino group, for example, dimethylamino and the like, a nitro group, a cyano group, a carboxyl group, an acyl group, for example, formyl, acetyl, and the like, an alkoxy group, for example, methoxy, ethoxy group, 2-methoxyethoxy, and the like, or, for example, a hydroxyl group; for example, a 1-methoxyethyl group, 2-(dimethylamino) ethyl group, benzyl group, 1-phenylethyl group, 2-phenylethyl group, 2-methoxyethyl group, 2-, 2-(2-methoxyethoxy)ethyl group, and the like. Examples of two alkyl groups forming a cyclic group are tetramethylene, pentamethylen, hexamethylene and di(2-ethoxy)ether group.

Preferably cations are tetramethylammonium, tetraethylammonium, tetrapropylammonium, tetra butylammonium, tetra-n-propylammonium, tetra-n-butylammonium, tetra-n-pentylammonium, tetra-n-hexyl ammonium, ethyl trimethylammonium, 2,2,2 trifluoroethyl trimethylammonium, 2,2,2 trifluoroethyl triethylammonium, ethyl tri(trifluromethyl) ammonium, methyl tri(trifluromethyl)ammonium, benzyltrimethylammonium, benzyltriethylammonium, trimethyl(2-methoxyethyl) ammonium, trimethyl[2-(2-methoxyethoxy)ethyl]ammonium, methyldiethyl-(2-methyoxyethyl) ammonium, triethyl (2-methyoxyethyl)ammonium, diethyl dimethylammonium, diethyl di(trifluromethyl)ammonium, diethyl methyl trifluromethylammonium, triethyl methylammonium, methyl tripropylammonium, ethyl tripropylammonium, trimethyl propylammonium, ethyl dimethyl propylammonium, yyy diethyl methyl propylammonium, triethyl propylammonium, dimethyl dipropylammonium, ethyl methyl dipropylammonium, diethyl dipropylammonium, trimethyl butylammonium, ethyl dimethyl butylv, diethyl methyl butylammonium, triethyl butylammonium, tripropyl butylammonium, dimethyl dibutylammonium, ethyl methyl dibutylammonium, diethyl dibutylammonium, spiro-1,1'-bipyrrolidinium, spiro-1,1'-bipiperidinium, spiro-1,1'-pyrrolidinium piperidinium, spiro-1,1'-pyrrolidinium morpholinium, spiro-1,1'-pyrrolidinium 2-methylmorpholinium, spiro-1,1'-pyrrolidinium 3-methylmorpholinium etc. Here, propyl includes n-propyl, i-propyl, butyl includes n-butyl, i-butyl, s-butyl, t-butyl. Particularly preferred cations include methyltriethylammonium, spiro-1,1'-bipyrrolidinium, spiro-1,1'-bipiperidinium, spiro-1,1'-pyrrolidinium piperidinium, spiro-1,1'-pyrrolidinium morpholinium, benzyltrimethylammonium, benzyltriethylammonium, trimethyl(2-methoxyethyl)ammonium, trimethyl[2-(2-methoxyethoxy)ethyl]ammonium etc. propylyltrimethylammonium, methyldiethyl-(2-methyoxyethyl)ammonium, triethyl (2-methyoxyethyl) ammonium, 2,2,2 trifluoroethyl trimethyl ammonium, 2,2,2 trifluoroethyl triethyl ammonium, spiro-1,1'-bipyrrolidinium and spiro-1,1'-bipiperidinium. In other preferred embodiments, the negatively charged anion Z is selected from the group consisting of $BF_4^-$, $PF_6^-$, $CF_3SO_3^-$ and $N(SO_2CF_3)_2^-$.

Compounds of the structure in Formula II are quaternary onium salts that, when dissolved in a solvent, form a negatively charged anion and an optionally substituted 6-member unsaturated heterocyclic cation, preferably having one nitrogen and five carbon ring members, such as pyridinium, 2-methylpyridinium, 3-methylpyridinium, 4-methylpyridinium, 2,6-dimethylpyridinium, quinolinium, isoquinolinium, acridinium or phenanthridinium;, or two nitrogen and four carbon ring members, such as pyridazinium, pyrimidium, pyrazinium or phenazinium; one nitrogen and one oxygen ring member, such as morpholinium, 2-methyl morpholinium or 3-methyl morpholinium. In certain embodiments, the functional groups attached to the ring atoms are independently fluorine, hydrogen or $C_1$-$C_{12}$ alkyls, preferably independently methyl, ethyl, propyl or butyl. In certain preferred embodiments, the cation is pyridinium and the anion is tetrafluoroborate.

Compounds of the structure in Formula III are quaternary onium salts that, when dissolved in a solvent, preferably form a negatively charged anion and an optionally substituted 5-member unsaturated heterocyclic cation, preferably having either one or two nitrogen ring members, such as pyrrolium, imidazolium, pyrazolium, indolium, isoindolium, quinazolinium or indozolium; three nitrogen ring members, such as triazolium, one nitrogen and one sulfur ring member, such as thiazolium, or one nitrogen and one oxygen ring member, such as oxazolium. In certain embodiments, the functional groups attached to the ring atoms are independently fluorine, hydrogen or $C_1$-$C_{12}$ alkyls, preferably independently methyl, ethyl, propyl or butyl. Even more preferably, the cation is diethylimidazolium, ethylmethylimidazolium, or butylmethylimidazolium and the anion is tetrafluoroborate, $CF_3SO_3^-$ or $N(SO_2CF_3)_2^-$ Compounds of the structure in Formula IV are quaternary onium salts that, when dissolved in a solvent, preferably form a negatively charged anion and an optionally substituted 5-member saturated heterocyclic cation, preferably having either one or two nitrogen ring members, such as pyrrolidinium, pyrazolidinium, imidazolidinium, indolinium, isoindolinium, three nitrogen ring members, such as triazolium, one nitrogen and one sulfur ring member, such as thiazolium, or one nitrogen and one oxygen ring member, such as oxazolium. In certain embodiments, the functional groups attached to the ring atoms are independently fluorine, hydrogen or $C_1$-$C_{12}$ alkyls, preferably independently methyl, ethyl, propyl, butyl or cyclic alkyls preferably independently pyrrolidinium, piperidinium or morpholinium thereby forming a spiro compound.

Even more preferably, the cation is diethylpyrrolidinium, ethylmethylpyrrolidinium, propylmethylpyrrolidinium, butylmethylpyrrolidinium, spiro-1,1'-bipyrrolidinium, spiro-1,1'-bipiperidinium, spiro-1-pyrrolidinium 1'-piperidinium or spiro-1-pyrrolidinium 1'-morpholinium and the anion is tetrafluoroborate.

Preferably, the salt solutions form an electrically conductive electrolyte. In certain preferred embodiments, the concentration of the onium salts in the non-aqueous solution is at least about 0.5 mol/L, more preferably at least about 1.0 mol/L.

Certain preferred salt solutions of the present invention comprise one of the above-described quaternary onium salts dissolved in at least one non-aqueous solvent. Certain other preferred salt solutions comprise a combination of at least two quaternary onium salts dissolved in at least one non-aqueous solvent. Particularly preferred combinations of salts include the combinations of imidazolium tetrafluoroborate and pyrazolium tetrafluoroborate; methyltriethylammonium tetrafluoroborate and ethylmethylimidazolium tetrafluoroborate; methyltriethylammonium tetrafluoroborate and ethylmethylimidazolium tetrafluoroborate; ethylmethylimidazolium tetrafluoroborate and ethylmethylpyrazolium tetrafluoroborate; and methyltriethylammonium tetrafluoroborate, ethylmethylimidazolium tetrafluoroborate and ethylmethylpyrazolium tetrafluoroborate.

The organic solvent in the non-aqueous solution is preferably at least one solvent selected from the group consisting of: an organic, cyclic carbonate, such as ethylene carbonate, propylene carbonate, butylene carbonate, and the like; an organic, linear carbonate such as dimethyl carbonate, ethyl methyl carbonate, diethyl carbonate, and the like; gamma-butylrolactone; sulfolane or some derivative thereof; nitrile, such as acetonitrile, propionitrile and the like; dinitrile, such as glutaronitrile, and the like; and combinations of these.

In certain embodiments, the concentration of halide in low purity quaternary onium salts could be above 20 weight percent. In many embodiments, low purity solutions having a halide content of not greater than about 5000 parts per million (ppm) are preferred, at least in part, because they allow for the present invention to occur in a compact system of columns. In certain embodiments, it is even more preferred that the low purity solutions have a halide content of from about 20 to about 2000 ppm. Quaternary onium salt solutions having a halide concentration of not greater than about 20 parts per million are generally considered pure, as that term is used herein, and are generally acceptable for products providing long life spans in accordance with preferred embodiments of the present invention.

Additionally, applicants have found that acidic impurities are critical for certain of the described applications. In some embodiments, the concentration of free acids in low purity quaternary onium salt liquids could be above 10 weight percent. Practically, the corresponding low purity liquids which have a free acid content of not greater than 5000 parts per million are preferred, at least in part, because they allow for the present invention to occur in a compact system of columns. Even more preferred are low purity solutions having a free acid content of from about 20 to about 2000 parts per million. Quaternary onium salt solutions having a free acid concentration of not greater than about 30 parts per million are generally considered pure, as that term is used herein, and are generally targeted to achieve long lifetime and non-corrosiveness in accordance with the present invention.

Another preferred step of the present invention is providing an ion exchange material charged with electrochemically stable anions.

Preferably, ion exchange materials are those which can exchange an ion (i.e. an atom or molecule that has lost or gained an electron and thus acquired an electrical charge) that is attached to the exchange material for a similarly charged ion from a solution. Ion exchange materials generally have greater selectivity for ions with increasing valence or charge. Among ions with the same charge, higher affinities are generally seen for ions with a higher atomic number. These affinity relationships are reversed in concentrated solutions, allowing for regeneration of the exchange material.

Ion exchange materials suitable for the present invention include, but are not limited to, materials that have immobile exchange sites and materials that have mobile exchange sites. Examples of suitable materials having immobile ion exchange sites include, but are not limited to, resins such as those forming a solid 3-dimensional polymer network that is essentially insoluble in the reaction media. Examples of suitable materials having mobile ion exchange sites include, but are not limited to liquid polycation salts that are essentially insoluble in the reaction media, such as polyammonium ionic liquid sulfonamides (PILS) and the like. Resins are generally preferred due to the ease at which the desired product can be separated from the exchange material.

Resins are typically synthetically produced solid organic particles in the form of beads that have a distinct number of immobile ion sites which set the maximum quantity of exchanges per unit of resin. Preferred resins according to the present invention are weakly basic anion and Type-1 strong base anion resins based upon a styrene-divinylbenzene (DVB) copolymer and having either a gel or macroporous physical structure. Gel resins are generally homogeneous crosslinked polymers having exchange sites evenly distributed throughout the bead. Macroporous resins have sponge-like structure of relatively larger pores than gel resins and therefore permit access to interior exchange sites. Although macroporous resins have better physical stability as compared to gels, gel resins typically have better operating efficiencies and cost less. Thus, a determination of the most appropriate resin will depend upon the particular application involved and one skilled in the art could readily make such a determination without undue experimentation in view of the teachings contained herein.

Ion exchange resins are preferably generally spherical in shape and, preferably, of substantially similar or uniform dimensions to accommodate the swelling and contraction of the resin bead during exhaustion and regeneration. Average bead diameter is preferably from about 2000 to about 250 µm, and more preferably from about 900 to about 250 µm.

Styrene-DVB resins according to the present invention can be manufactured by processes known in the art. These resins are also commercial available as, for example, Dow Chemical's DOWEX 21K Cl, DOWEX 21K XLT, DOWEX M43 and Marathon WBA; Rohm & Haas' Amberjet 4200; Amberjet 4600 Cl; Amberlite IRA-67, Amberlite IRA-96, Amberlite IRA-743, Amberlite IRA-900 Cl, Amberlyst A21, Duolite A7; and Lanxess' Lewatit Monoplus M500, MP-62 and MP-64.

For the halide reduction step the resin is preferably charged before use with anions. This charging process imparts negatively charged ions to the resin which are then available for exchange with similarly charged ions in the salt solution to be purified. Therefore, the solution utilized in this process preferably supplies anions to the resin that are more electrochemically stable than the halide ion impurities which are sought to be removed from the salt solution. In certain preferred embodiments, the resin is charged with acid solution, wherein the acid anions attach to the resin.

For the free acid reduction step the resin is in case of a weakly basic resin type not charged before use or in the case of chloride containing strong base resin types conditioned with e.g. caustic soda, water and an appropriate solvent. Therefore, the resin utilized in this process preferably removes free acid from the solution via an adsorption.

The ion exchange resins may be provided in any configuration adaptable for use with the present invention. For example, in certain preferred embodiments, these resins are provided in one or, more preferably, multiple ion exchange columns that can be arranged in parallel or, more preferably, in series. Other embodiments of the present invention include resins that are provided in fixed or fluid ion exchange beds.

The present invention also comprises in preferred embodiments, the step of contacting the salt solution with the ion exchange material to produce a quaternary onium salts solution having a second concentration of halide which is less than the first concentration of halide.

Figure 5:
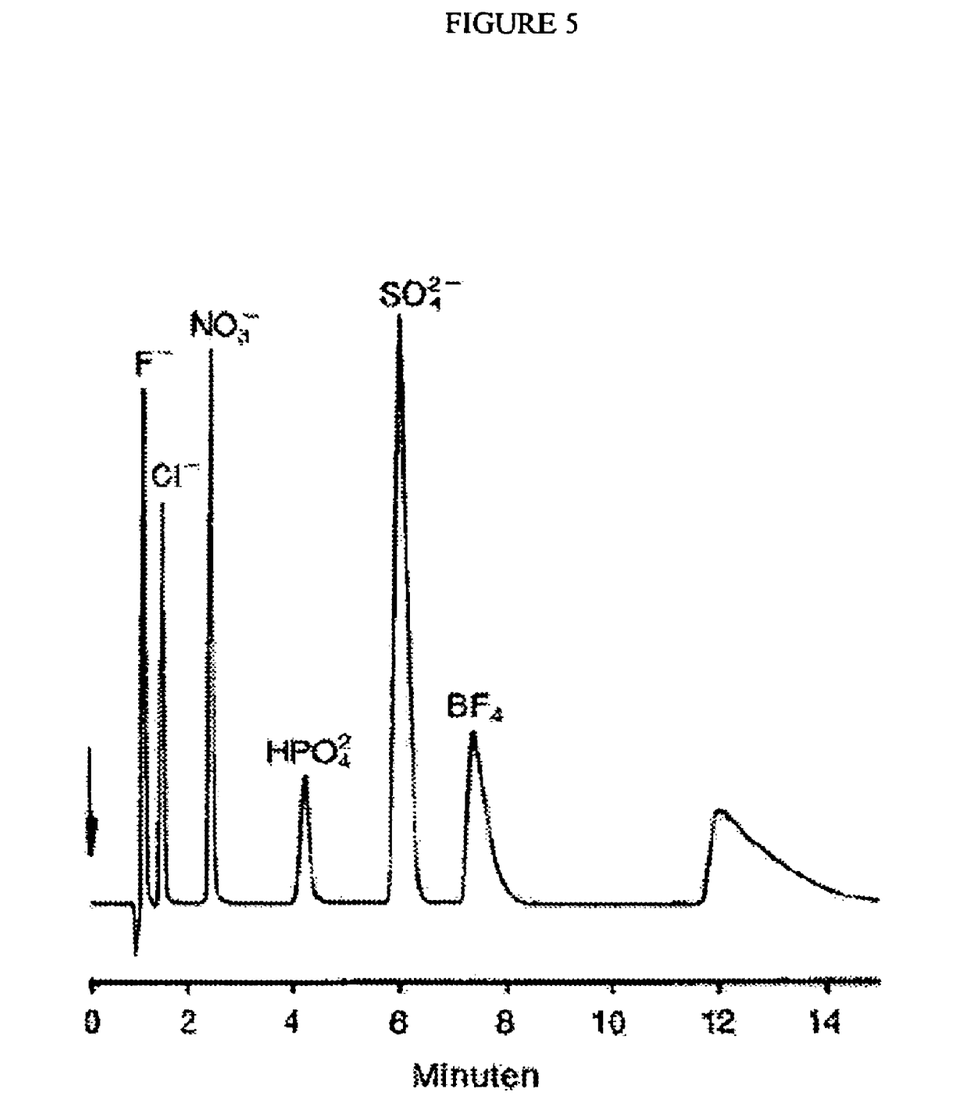
FIG. 5 depicts an ion chromatogram illustrating the separation of inorganic anions and the order of elution (Joachim Weiss, Ionenchromatographie, 2. reprint 1991, ISBN 3-527-28236-x).

Preferably, the ion exchange material has a greater selectivity for more electrochemically stable ions, such as tetrafluoroborate, than the halide ions which are to be removed. Although applicants do not intend to be bound by or to any particular theory of operation, it is believed that for ions having the same charge, the exchange material tends to favor ions having a higher atomic number or a larger size. Referring to FIG. 5, ion chromatography of anions in an aqueous solution shows that weakly adsorbed anions are eluated earlier than strongly adsorbed anions. The graph illustrates that fluoride is first eluated, followed by chloride, nitrate, monohydrogenphosphate, sulfate, tetrafluoroborate, and iodide. Therefore, chloride will not be adsorbed in the presence of an excess of tetrafluoroborate and, thus, chloride can generally not be eliminated from an aqueous solution containing tetrafluoroborate. Likewise, fluoride can generally not be adsorbed in the presence of an excess of tetrafluoroborate due to the in-situ formation of hydrolyzing tetrafluoroborate anions.

Unexpectedly, however, according to preferred aspects of the present invention, anion exchange materials have a greater affinity for halide ions if the exchange is carried out in a non-aqueous solution. This unexpected property allows reversal of the exchange direction so that the exchange materials remove halide anions from the salt solutions, even when the halide anions are present in very low concentrations.

In certain preferred embodiments, the halide concentration of the purified salt solution (i.e. the second concentration) is less than about 10 percent of the concentration of the crude salt solution (i.e. the first concentration). In other preferred embodiments, the second concentration of halide in the salt solution is less than about 100 parts per million by weight, more preferably less than about 5 parts per million by weight, and even more preferably less than about 1 parts per million by weight. Additionally, in certain preferred embodiments, steps (a) through (c) of the present invention may be repeated one or more times to iteratively reduce the halide concentration in the salt solution. Preferably, these steps are repeated once, and more preferably, these steps are repeated two or more times.

The halide exchange efficiency for salt solutions comprising a non-aqueous solvent in accordance with the present invention is generally higher if the salt solution has a residual water content of not greater than about 1000 parts per million by weight. Therefore, in certain preferred embodiments, the salt solution in the exchange process has a residual water content of not greater than about 5 weight percent, more preferably not greater than about 1000 ppm. As used herein, the term "residual water" refers to the water content in the polymer network of the ion exchange resin. For such embodiments, at least a portion of the residual water may be optionally removed by a drying process before or during the step of reducing halide ion concentration. Several drying processes known in the art are amenable to the present invention, including molecular sieves drying or azeotropic distillation.

The purified salt solution can be further diluted or concentrated by ordinary methods or used as it is e.g. to fill electrochemical cells or to work as reaction media in chemical synthesis reactions or the purified salt can be isolated by removing the solvent from the solution.

The reduction of ionic impurities can be run as a batch process, usually as a multistep, or as a continuous process, usually with column equipment known by people skilled in the art. Further the reduction steps can be carried out separately or in series, e.g. lead-lag or merry-go-round set-up. The procedure requires at least one type of resin being appropriately conditioned.

EXAMPLES

The following examples illustrate and exemplify certain preferred embodiments of the present invention but are not intended to limit in any way the broad scope of the invention.

Examples 1-3 and Comparative Example A

Preparation of the Charged Anion Exchange Resin:

100 g of charged styrene macroporous anion exchange resin (sold under the trade designation DOWEX M-43) is provided. This resin is brought into intimate contact with 300 ml fluoroboric acid (concentration: 10%) by adding the resin to the solution and mixing for one hour. The liquid was then separated from the resin. A new 300 g batch of fluoroboric acid (concentration: 10%) is provided, added, and mixed as before to the resin from the first separation step. The liquid from the second mixing step is then separated from the resin. After the second separation, the resin is washed with 250 ml of water four times. The pH of the last washing water was 6. The resin was dried for several days under vacuum and temperature up to 40° C.

Ion Exchange:

In a glovebox with a dry and oxygen free argon atmosphere, 300 g of a 1 molar solution of tetraethylammonium tetrafluoroborate (TEA-BF$_4$) in acetonitrile containing impurities (as described in WO 2004/039761) and a water content of 292 parts per million is stirred for 1 hour with 5.6 g of the charged anion exchange resin prepared as described above. The TEA-BF$_4$ solution is then removed from the solid anion exchange resin and a sample of the solution is taken and dried to the desired water content below 20 ppm. The final moisture content of the solution is determined by a Karl-Fisher titration method and the halide content is determined by ion chromatography.

To evaluate the sample solution's electrochemical stability, the sample is subjected to cyclic voltammetry (CV) to determine its "voltage window". To determine the voltage window, the sample is placed in a cell having a working electrode, a counter electrode, and a test electrode, which is immediately adjacent but not touching the working electrode. The electrodes in the cell are connected to an apparatus applying cyclic voltage, called a potentiostat, which is configured to adjust the current between the working and counter electrodes to maintain a "desired voltage" between the working electrode and the reference electrode. The voltage between the reference electrode and the working electrode can be varied as a function of time in a programmed manner. The voltage window is determined by progressively increasing the desired voltage (in both the positive and negative directions) until there is a precipitous increase in the current required to drive the working and counter electrodes to maintain the desired voltage. The sharp rise in current at the end voltages generally indicates the breakdown voltage of the electrolyte solution, meaning that the salt or the solvent is undergoing an irreversible, destructive reduction reaction at the negative end voltage or an oxidation reaction at the positive end voltage.

This ion exchange procedure is iteratively repeated a second and a third time with the solution. Samples are taken each time, dried and characterized in the same way.

The reference material was prepared from the same raw material in an identical way except that it is not treated with any anion exchange resin before drying.

Figure 1:
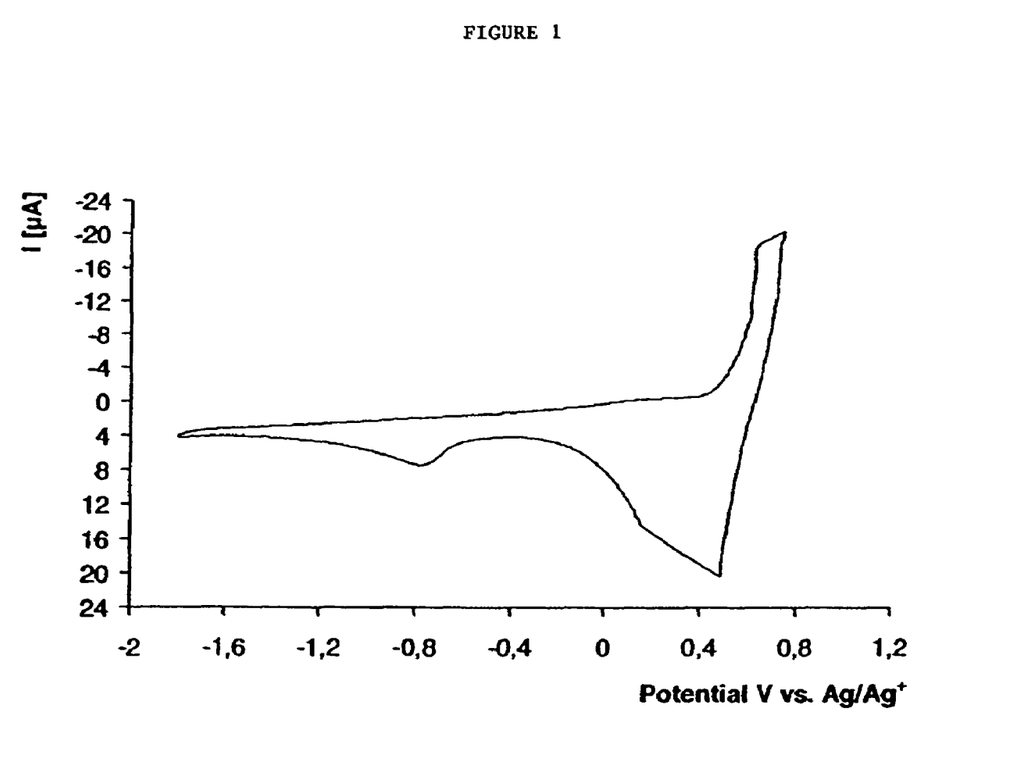
FIG. 1 depicts a cyclic voltammogram for a non-aqueous quaternary onium salt solution reference containing chloride as an impurity.
Figure 2:
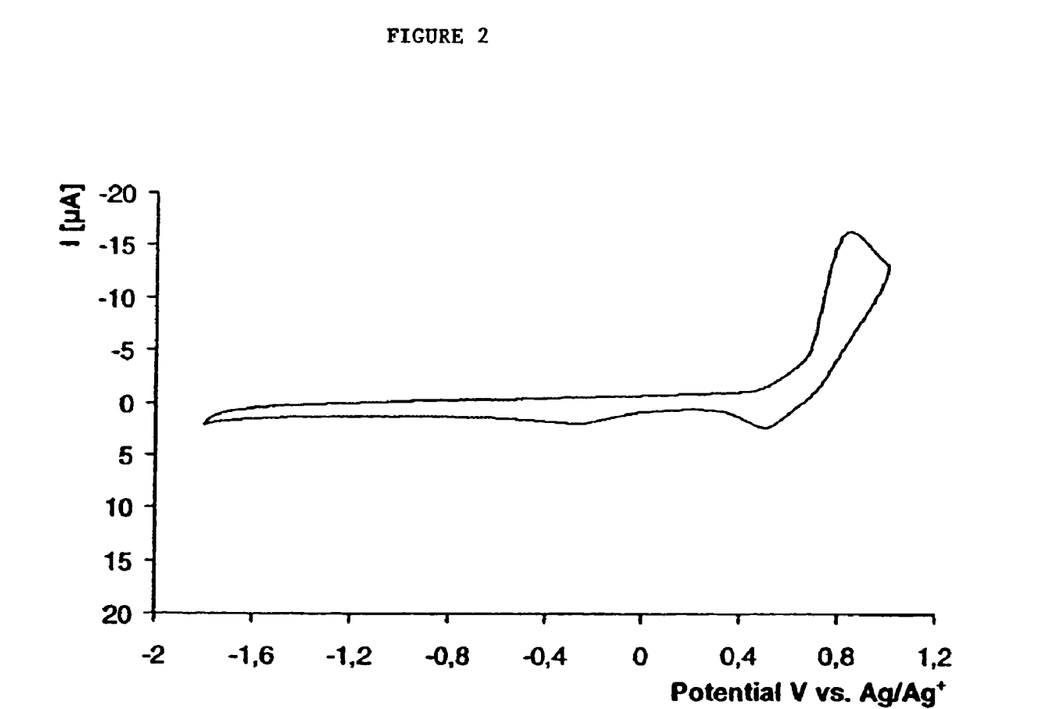
FIG. 2 depicts a cyclic voltammogram for the salt solution reference after one treatment with anion exchange materials according to the present invention.
Figure 3:
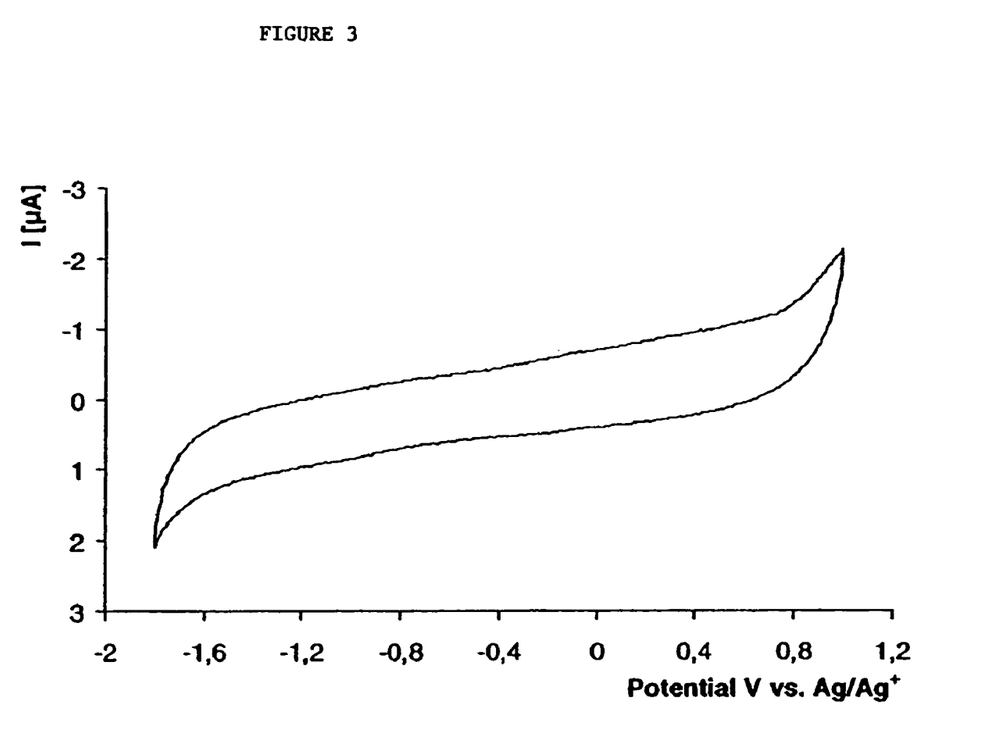
FIG. 3 depicts a cyclic voltammogram for the salt solution reference after two treatments with anion exchange materials according to the present invention.
Figure 4:
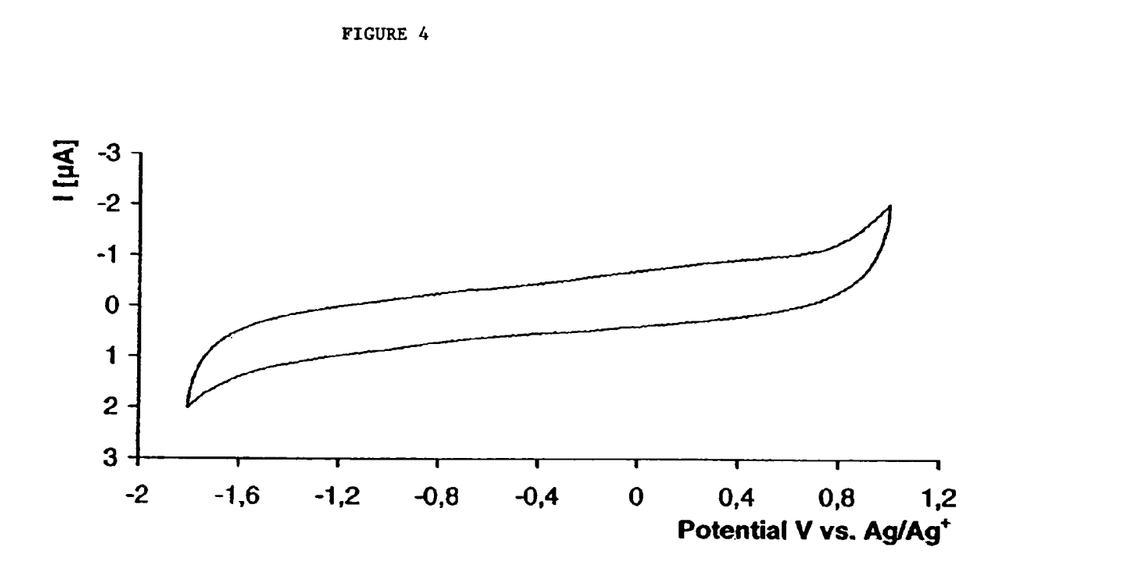
FIG. 4 depicts a cyclic voltammogram for the salt solution reference after three treatments with anion exchange materials according to the present invention.

| Example | Iteration | Cl content [ppm] | F content [ppm] | Br content [ppm] | CV |
|---|---|---|---|---|---|
| Comparative (A) | Reference | 670 | 229 | 637 | Peak (See FIG. 1) |
| 1 | One treatment | 33 | 49 | 58 | Peak (See FIG. 2) |
| 2 | Two treatment | <10 | 26 | 12 | No Peak (See FIG. 3) |
| 3 | Three treatment | <10 | <10 | <10 | No Peak (See FIG. 4) |

As shown in the table above, the resin concurrently reduces the concentration of F, Cl, and Br. However, it is understood that the methods of the present invention are not limited to reducing only these ions, but in fact can reduce all halide ions as well as sulfate.

Examples 4-6

Preparation of Strongly Basic Scavenger Resin:

100 g of charged styrene macroporous anion exchange resin (sold under the trade designation Amberjet 4600 Cl) is provided. This resin is brought into intimate contact with 300 ml caustic soda (concentration: 5%) by adding the resin to the solution and mixing for one hour. The liquid was then separated from the resin. A new 300 ml batch of caustic soda (concentration: 5%) is provided, added, and mixed as before to the resin from the first separation step. The liquid from the second mixing step is then separated from the resin. After the second separation, the resin is washed with 250 ml of water four times. The resin was washed with 300 ml of an organic solvent, e.g. acetonitrile and dried for several days under vacuum and temperature up to 40° C.

Preparation of Weakly Basic Acid Scavenger Resin:

100 g of charged styrene gel anion exchange resin (sold under the trade designation Duolite A7) is provided. This resin is washed with 250 ml of water four times. The resin was washed with 300 ml of an organic solvent, e.g. acetonitrile and dried for several days under vacuum and temperature up to 40° C.

Free Acid Reduction:

In a glovebox with a dry and oxygen free argon atmosphere, 300 g of a 1 molar solution of tetraethylammonium tetrafluoroborate (TEA-$BF_4$) in acetonitrile containing impurities (as described in WO 2004/039761, which is incorporated herein by reference) and a water content of 292 parts per million is stirred for 1 hour with 5.6 g of the weakly basic anion exchange resin prepared as described above. The TEA-$BF_4$ solution is then removed from the resin and a sample of the solution is taken and dried to the desired water content below 20 ppm. The final moisture content of the solution is determined by a Karl-Fisher titration method and the free acid content is determined by titration. As shown in the table below, the resin concurrently reduces the concentration of free acid.

| Example | Iteration | Free acid content [ppm] |
|---|---|---|
| Comparative (A) | Reference | 957 |
| 4 | One treatment | 52 |
| 5 | Two treatments | <10 |
| 6 | Three treatments | <10 |

Examples 7-9 and Comparative Example B

The above process is repeated, except that the anion exchange resin is dried by extracting the water by washing it with a sufficient volume of anhydrous acetonitrile.

| Example | Iteration | Cl content [ppm] | CV |
|---|---|---|---|
| Comparative (B) | Reference | 670 | Peak |
| 7 | One treatment | 33 | Peak |
| 8 | Two treatment | <10 | No Peak |
| 9 | Three treatment | <10 | No Peak |

Examples 10-13

The process for Example 3 is repeated (three treatments), except that the TEA-$BF_4$ solution for the anion exchange process contains different concentrations of water during the exchange process.

| Example | Water concentration | CV |
|---|---|---|
| 10 | 5 wt. % | No Peak, shoulder |
| 11 | 2000 ppm | No Peak |
| 12 | 500 ppm | No Peak |
| 13 | 50 ppm | No Peak |

The examples demonstrate that different water concentrations during the exchange process do not change the selectivity of BF4 replacement on the resin verses the chloride.

Examples 14-16 and Comparative Example C

The process for Examples 1-3 is repeated, except that the TEA-BF$_4$ solution for the anion exchange process is dried so that it contains less than 20 parts per million of water prior to being stirred with the resin.

| Example | Iteration | Cl content [ppm] | CV |
|---|---|---|---|
| Comparative C | Reference | 670 | Peak |
| 14 | One treatment | 209 | Peak |
| 15 | Three treatment | 72 | Peak |
| 16 | Four treatment | <10 | No Peak |

The examples demonstrate that the ion exchange reactivity at a water content of 20 parts per million is lower than the ion exchange reactivity at a water content of 500 ppm.

Examples 17-30

The process for Example 3 is repeated, except that different anion exchange resins are utilized.

| Example | Resin | Structure | Function | Delivery Form | CV |
|---|---|---|---|---|---|
| 17 | Amberjet 4200 | Gel | Strong Base | OH | No Peak |
| 18 | Amberjet 4600 Cl | Gel | Strong Base | Chloride | No Peak |
| 19 | Amberlite IRA-67 | Gel | Weak Base | Free base | No Peak |
| 20 | Amberlite IRA-96 | Macroreticular | Weak Base | Free base | No Peak |
| 21 | Amberlite IRA-743 | Macroreticular | Weak Base | Free base | No Peak |
| 22 | Amberlite IRA-900 Cl | Macroporous | Strong Base | Chloride | No Peak |
| 23 | Amberlyst A21 | Macroreticular | Weak Base | Free base | No Peak |
| 24 | Duolite A7 | Very porous | Weak Base | Free base | No Peak |
| 25 | DOWEX 21K Cl | Gel | Strong Base | Chloride | No Peak |
| 26 | DOWEX 21K XLT | Gel | Strong Base | OH | No Peak |
| 27 | DOWEX M43 | Macroporous | Weak Base | Free base | No Peak |
| 28 | Lewatit Monoplus M500 | Gel | Strong Base | OH | No Peak |
| 29 | Lewatit MP-62 | Macroporous | Weak Base | Free base | No peak |
| 30 | Lewatit MP-64 | Macroporous | Weak Base | Free base | No peak |

The examples demonstrate that the ion exchange process is not limited to a specific ion exchange resin.

Examples 31-33

The process for example 1 is repeated, except that instead of stirring the TEA-BF$_4$ solution for 1 hour with 5.6 g of the charged anion exchange resin, the solution is passed through a 250 ml ion exchange column at various flow rates.

| Example | Flow Rate | CV |
|---|---|---|
| 31 | 100 ml/min. | Peak |
| 32 | 50 ml/min. | Peak |
| 33 | 5 ml/min. | No Peak |

The examples demonstrate that the ion exchange process can be carried out in batch or continues process.

Examples 34-36

The process for example 3 is repeated, except that various concentrations of TEA-BF$_4$ solution are mixed with the charged anion exchange resin.

| Example | TEA-BF$_4$ Molarity | CV |
|---|---|---|
| 34 | 0.5 | No Peak |
| 35 | 1.0 | No Peak |
| 36 | 1.5 | No Peak |

The examples demonstrate that ion exchange process can be carried out in the presence of high concentrations of concurring BF4 anions.

Examples 37-39

The process for example 3 is repeated, except that solvents other than acetonitrile are used to prepare the TEA-BF$_4$ solution.

| Example | Solvent | CV |
|---|---|---|
| 37 | Propylene Carbonate | No Peak |
| 38 | Gamma-butyrolactone | No Peak |
| 39 | Sulfolane | No Peak |

The examples demonstrate that ion exchange process can be carried out in acetonitrile-free solution.

Examples 40-58

The process for example 3 is repeated, except that salts other than TEA-BF$_4$ are utilized in preparation of the electrolyte solution.

| Example | Salt | CV |
|---|---|---|
| 40 | methyltriethylammonium tetrafluoroborate | No Peak |
| 41 | tetraethylammonium hydrogen maleate | No Peak |
| 42 | pyridinium tetrafluoroborate | No Peak |
| 43 | 50% methyltriethylammonium tetrafluoroborate/ 50% tetraethylammonium tetrafluoroborate | No Peak |
| 44 | Ethylmethylimidazolium tetrafluoroborate | No Peak |
| 45 | Butylmethylimidazolium tetrafluoroborate | No Peak |
| 46 | 50% methyltriethylammonium tetrafluoroborate/ 50% ethylmethylimidazolium tetrafluoroborate | No Peak |
| 47 | 50% ethylmethylimidazolium tetrafluoroborate/ 50% ethylmethylpyrazolium tetrafluoroborate/ | No Peak |
| 48 | 50% methyltriethylammonium tetrafluoroborate/ 25% ethylmethylimidazolium tetrafluoroborate/ 25% ethylmethylpyrazolium tetrafluoroborate/ | No Peak |
| 49 | 2,2,2-trifluoroethyltrimethylammonium tetrafluoroborate | No Peak |
| 50 | di-(2,2,2-trifluoroethyl) dimethylammonium tetrafluoroborate | No Peak |
| 51 | di-(2,2,2-trifluoroethyl) dipropylammonium tetrafluoroborate | No Peak |
| 52 | benzyltrimethylammonium tetrafluoroborate | No Peak |
| 53 | trimethyloctylammonium tetrafluoroborate | No Peak |
| 54 | 50% methyltriethylammonium tetrafluoroborate/ 50% spiro-1,1'-b ipyrrolidinium tetrafluoroborate | No Peak |
| 55 | Trimethyl (2-methoxyethyl)ammonium tetrafluoroborate | No Peak |
| 56 | 1-ethyl-1-methylpyrrolidinium tetrafluoroborate | No Peak |
| 57 | 1-methyl-1-propyl-pyrrolidinium tetrafluoroborate | No Peak |
| 58 | 1,1-diethyl pyrrolidinium tetrafluoroborate | No Peak |
| 59 | Tetraethylammonium trifluoromethyltrifluoroborate | No Peak |
| 60 | Tetraethylammonium bis(trifluoromethyl)difluoroborate | No Peak |
| 61 | Tetraethylphosphonium trifluoromethyltrifluoroborate | No Peak |

The examples demonstrate that ion exchange process can be carried out with different quarterny onium salt solutions.

Having thus described a few particular embodiments of the invention, various alterations, modifications, and improvements will readily occur to those skilled in the art. Such alterations, modifications, and improvements, as are made obvious by this disclosure, are intended to be part of this description though not expressly stated herein, and are intended to be within the spirit and scope of the invention. Accordingly, the foregoing description is by way of example only, and not limiting. The invention is limited only as defined in the following claims and equivalents thereto.

What is claimed is:

1. A method of purifying quaternary onium salts comprising the step of contacting a composition comprising an organic solvent-based onium salt solution, wherein said onium salt comprises one or more anions selected from the group consisting of $BF_4^-$, $[BF_x(C_yF_{2y+1-z}H_z)_{4-x}]_n^-$ in which the ligands $(C_yF_{2y+1-z}H_z)$ may be identical or different, $1<x<3$, $1 \leq y \leq 8$ and $0 \leq z \leq 2y+1$, $PF_6^-$, $[PF_x(C_yF_{2y+1-z}H_z)_{6-x}]^-$ in which in which the ligands $(C_yF_{2y+1-z}H_z)$ may be identical or different, $1 \leq x \leq 5$, $3 \leq y \leq 8$ and $0 \leq z \leq 2y+1$, $CF_3SO_3^-$, $SbF_6^-$, $N(SO_2CF_3)_2^-$, $C_4H_3O_4^-$, and $ClO_4^-$ and a first concentration of halide ionic impurities with an ion exchange material to produce a composition comprising a quaternary onium salt and a second concentration of halide ionic impurities, wherein said second concentration of halide ionic impurities is less than said first concentration of halide ionic impurities.

2. The method of claim 1 wherein said salt comprises one or more cations having the formula $(R^aR^bR^cR^d)A^+$, wherein:
A is P or N
$R^a$, $R^b$, $R^c$, and $R^d$ are independently a $C_1$-$C_{12}$ alkyl, a member of a $C_2$-$C_{20}$ unsaturated cyclic or heterocyclic, or a single, double, or non-localized pi bond, provided that a combination of bonds result in a tetravalent N or P.

3. The method of claim 1 wherein said salt comprises one or more cations having the formula $[A^+R_4][Z^-]$, wherein Z is said anion and A is trivalent atom such as nitrogen or phosphorous; R is independently a substituted or un-substituted $C_1$-$C_{12}$ alkyl, a substituted or un-substituted fluoroalkyl, or a member of a 5- or 6-member saturated, unsaturated, or aromatic cyclic or heterocyclic, or a member of a polycyclic structure.

4. The method of claim 1 wherein said quaternary onium salt has the formula:

wherein:
A is nitrogen or phosphorous;
$R^1$-$R^4$ are independently $C_1$-$C_{12}$ alkyl; and
Z is said anion.

5. The method of claim 4 wherein $R^1$, $R^2$, $R^3$, and $R^4$ are independently selected from the group consisting of methyl, ethyl, propyl, 2,2,2 trifluoroethyl, 2-methoxyethyl and tetramethylene.

6. The method of claim 5 wherein the cation of said quaternary onium salt is selected from the group consisting of trimethylethylammonium, tetraethylammonium, ethyl dimethyl propylammonium, methyldiethyl-(2-methyoxyethyl) ammonium, spiro-1,1'-bipyrrolidinium and combinations of these.

7. The method of claim 1 wherein said quaternary onium salt has the formula:

wherein
A is nitrogen or phosphorous;
n is independently 0 or 1;
$R_{10}$ is a substituted or unsubstituted $C_1$-$C_{12}$ alkyl, substituted or unsubstituted fluoroalkyl, member of a five or six member saturated, unsaturated, or aromatic heterocyclic structure, or member of a polycyclic structure;
$R_5$-$R_9$ are independently H, F, Cl, substituted or unsubstituted $C_1$-$C_{12}$ alkyl, substituted or unsubstituted fluoroalkyl, member of a five or six member saturated, unsaturated, or aromatic heterocyclic structure, or member of a polycyclic structure (e.g., spiro-, condensated-, or bridged-structure, or some combination thereof);
$D_1$-$D_5$ are independently carbon, nitrogen, sulfur, or oxygen provided that:

at least three of $D_1$-$D_5$ are carbon;
when a D ring member is carbon, n is 1 for its corresponding R group;
when a D ring member is nitrogen, oxygen, or sulfur, n is 0 for its corresponding R group;
the bond between any two adjacent D members is single, double, or aromatic;
the bond between A and either of its two adjacent D members is single, double, or aromatic provided that A is tetravalently bonded; and
Z is a said anion.

8. The method of claim 7 wherein $R_5$-$R_{10}$ are independently selected from the group consisting of hydrogen, methyl, ethyl, propyl, 2,2,2 trifluoroethyl, 2-methoxyethyl and tetramethylene.

9. The method of claim 7 comprising substituted or unsubstituted pyridinium cations.

10. The method of claim 7 wherein Z is $BF_4^-$.

11. The method of claim 1 wherein said quaternary onium salt has the formula:

wherein
A is nitrogen or phosphorous;
n is independently 0 or 1;
$R_{15}$ is a substituted or unsubstituted $C_1$-$C_{12}$ alkyl, substituted or unsubstituted fluoroalkyl, member of a five or six member saturated, unsaturated, or aromatic heterocyclic structure, or member of a polycyclic structure;
$R_{11}$-$R_{14}$ are independently H, F, Cl, substituted or unsubstituted $C_1$-$C_{12}$ alkyl, substituted or unsubstituted fluoroalkyl, member of a five or six member saturated, unsaturated, or aromatic heterocyclic structure, or member of a polycyclic structure;
$D_6$-$D_9$ are independently carbon, nitrogen, sulfur, or oxygen provided that:
at least two of $D_6$-$D_9$ are carbon;
when a D ring member is carbon, n is 1 for its corresponding R group;
when a D ring member is nitrogen, oxygen, or sulfur, n is 0 for its corresponding R group;
the bond between any two adjacent D members is single, double, or aromatic;
the bond between A and either of its two adjacent D members is single, double, or aromatic provided that A is tetravalently bonded; and
Z is said anion.

12. The method of claim 11 wherein $R_{11}$-$R_{15}$ are independently selected from the group consisting of hydrogen, methyl, ethyl, propyl, butyl, 2,2,2 trifluoroethyl, 2-methoxyethyl, tetramethylene and pentamethylene.

13. The method of claim 11 wherein the cation of the said quaternary onium salt is selected from the group consisting of substituted or unsubstituted imidazolium cations, substituted or unsubstituted pyrazolium cations, and combinations of these.

14. The method of claim 13 wherein said imidazolium cations are selected from the group consisting of dimethylimidazolium, ethylmethylimidazolium, butylmethylimidazolium, and combinations of these.

15. The method of claim 14 wherein said pyrazolium cations are selected from the group consisting of dimethyl pyrazolium, ethylmethyl pyrazolium, butylmethyl pyrazolium, and combinations of these.

16. The method of claim 1 wherein said quaternary onium salt has the formula:

wherein
A is nitrogen or phosphorous;
n and m are independently 0 or 1;
$R_{24}$ and $R_{25}$ are independently a substituted or unsubstituted $C_1$-$C_{12}$ alkyl, substituted or unsubstituted fluoroalkyl, member of a five or six member saturated, unsaturated, or aromatic heterocyclic structure, or member of a polycyclic structure (e.g., spiro-, condensated-, or bridged-structure, or some combination thereof);
$R_{16}$ and $R_{23}$ are independently H, F, Cl, substituted or unsubstituted $C_1$-$C_{12}$ alkyl, substituted or unsubstituted fluoroalkyl, member of a five or six member saturated, unsaturated, or aromatic heterocyclic structure, or member of a polycyclic structure (e.g., spiro-, condensated-, or bridged-structure, or some combination thereof);
$D_{10}$-$D_{13}$ are independently carbon, nitrogen, sulfur, or oxygen provided that:
at least two of $D_{10}$-$D_{13}$ are carbon;
when a D ring member is carbon, n and m are 1 for their corresponding R groups;
when a D ring member is nitrogen, n is 1 and m is 0 for their corresponding R groups;
when a D ring member is oxygen or sulfur, n and m are 0 for their corresponding R groups;
Z is said anion.

17. The method of claim 16 wherein $R_{16}$-$R_{25}$ are independently selected from the group consisting of hydrogen, methyl, ethyl, propyl, butyl, 2,2,2 trifluoroethyl, 2-methoxyethyl, tetramethylene and pentamethylene.

18. The method of claim 16 comprising substituted or unsubstituted pyrrolidinium cations.

19. The method of claim 18 wherein said pyrrolidinium cations are selected from the group consisting of dimethyl pyrrolidinium, ethylmethyl pyrrolidinium, propylmethyl pyrrolidinium, butylmethyl pyrrolidinium, diethyl pyrrolidinium, propylethyl pyrrolidinium, butylethyl pyrrolidinium, butyipropyl pyrrolidinium, spiro-1,1'-bipyrrolidinium, spiro-1,1'-bipiperidinium, spiro-1-pyrrolidinium 1'-piperidinium or spiro-1-pyrrolidinium 1'-morpholinium and combinations of these.

20. The method of claim 1 wherein said quaternary onium salt comprises a combination of quaternary onium cations.

21. The method of claim 20 wherein said quaternary onium salt comprises a combination of imidazolium tetrafluoroborate and pyrazolium tetrafluoroborate.

22. The method of claim 20 wherein said quaternary onium salt comprises a combination selected from the group consisting of methyltriethylammonium tetrafluoroborate and ethylmethylimidazolium tetrafluoroborate;

methyltriethylammonium tetrafluoroborate and ethylmethylimidazolium tetrafluoroborate; ethylmethylimidazolium tetrafluoroborate and ethylmethylpyrazolium tetrafluoroborate; and methyltriethylammonium tetrafluoroborate, ethylmethylimidazolium tetrafluoroborate and ethylmethylpyrazolium tetrafluoroborate.

23. The method of claim 1 wherein said salt solution comprises a solvent selected from the group consisting of nitrile, dinitrile, cyclic carbonate, linear carbonate, gamma-butyrolactone, sulfolane, sulfolane derivates, and combinations of these.

24. The method of claim 23 wherein said solvent is selected from the group consisting of ethylene carbonate, propylene carbonate, butylene carbonate, dimethyl carbonate, ethyl methyl carbonate, diethyl carbonate, gamma-butlyrolactone, sulfolane, acetonitrile, propionitrile, glutaronitrile, and combinations of these.

25. The method of claim 24 wherein said quaternary onium salt solution has a salt concentration of at least about 0.5 mol/L.

26. The method of claim 24 wherein said quaternary onium salt solution has a salt concentration of at least about 1.0 mol/L.

27. The method of claim 1 wherein said ionic impurity is selected from the group consisting of fluoride ion, chloride ion, bromide ion, iodide ion, and combinations of these.

28. The method of claim 1 wherein said ionic impurity comprises a combination of chloride ion, bromide ion, and combinations of these.

29. The method of claim 1 wherein said ion exchange material comprises immobile ion exchange sites.

30. The method of claim 1 wherein said ion exchange material comprises mobile ion exchange sites.

31. The method of claim 29 wherein said ion exchange material is a resin.

32. The method of claim 29 wherein said ion exchange material is a weak-base anion or strong-Type-1 base anion exchange resin.

33. The method of claim 29 wherein said ion exchange resin is a styrene-divinylbenzene-based polymer.

34. The method of claim 29 wherein said ion exchange material is a macroporous resin.

35. The method of claim 31 wherein resin is a gel.

36. The method of claim 31 wherein said resin is packed in a plurality of columns arranged in series.

37. The method of claim 1 wherein said first ionic impurity concentration is from about 20 parts per million by weight to about 20 weight percent.

38. The method of claim 37 wherein said first ionic impurity concentration is from about 20 weight-percent to about 5000 parts per million by weight.

39. The method of claim 37 wherein said first ionic impurity concentration is from about 20 to about 2000 parts per million by weight.

40. The method of claim 1 wherein said second ionic impurity concentration is less than about 10 percent of said first halide concentration.

41. The method of claim 39 wherein said second ionic impurity concentration is less than about 100 parts per million by weight.

42. The method of claim 41 wherein said second ionic impurity concentration is less than about 5 parts per million by weight.

43. The method of claim 42 wherein said second ionic impurity concentration is less than about 1 parts per million by weight.

44. The method of claim 1 wherein said quaternary onium salt solution has an original residual water content between about 10 parts per million and about 5 percent weight when in contact with the ion exchange resin.

45. The method of claim 44 wherein said quaternary onium salt solution has an residual water content between about 50 parts per million and about 5000 parts per million percent weight during the ion exchange process.

46. The method of claim 45 wherein said quaternary onium salt solution has an residual water content between about 100 parts per million and about 1000 parts per million percent weight during the ion exchange process.

47. The method of claim 44 wherein said water content is reduced subsequent to said contacting step.

48. The method of claim 1 wherein said contacting step is repeated to iteratively reduce said second ionic impurity concentration.

49. A method of isolating a quaternary onium salt comprising the steps of:
(a) purifying a quaternary onium salt according to the method of claim 1; and
(b) removing said solvent to isolate the purified salt.

* * * * *

UNITED STATES PATENT AND TRADEMARK OFFICE
CERTIFICATE OF CORRECTION

PATENT NO. : 7,601,871 B2  Page 1 of 1
APPLICATION NO. : 11/368168
DATED : October 13, 2009
INVENTOR(S) : Siggel et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 456 days.

Signed and Sealed this

Fifth Day of October, 2010

David J. Kappos
*Director of the United States Patent and Trademark Office*